(12) United States Patent
Shang

(10) Patent No.: US 10,695,578 B1
(45) Date of Patent: Jun. 30, 2020

(54) VASCULAR OPTICAL FIBER GUIDEWIRE WITH PLUG

(71) Applicant: Hua Shang, Jiangsu Province (CN)

(72) Inventor: Hua Shang, Jiangsu Province (CN)

(*) Notice: Subject to any disclaimer, the term of this patent is extended or adjusted under 35 U.S.C. 154(b) by 0 days.

(21) Appl. No.: 16/849,130

(22) Filed: Apr. 15, 2020

Related U.S. Application Data

(63) Continuation of application No. PCT/CN2019/105100, filed on Sep. 10, 2019.

(30) Foreign Application Priority Data

Aug. 9, 2019 (CN) .......................... 2019 1 0735056

(51) Int. Cl.
*A61N 5/06* (2006.01)
*G02B 6/38* (2006.01)
*A61B 17/00* (2006.01)

(52) U.S. Cl.
CPC ........... *A61N 5/0601* (2013.01); *A61N 5/062* (2013.01); *G02B 6/3859* (2013.01); *A61B 2017/00477* (2013.01); *A61B 2017/00867* (2013.01); *A61N 2005/0602* (2013.01); *A61N 2005/063* (2013.01)

(58) Field of Classification Search
CPC .................................................... G02B 6/3859
See application file for complete search history.

(56) References Cited

U.S. PATENT DOCUMENTS

| | | | | |
|---|---|---|---|---|
| 5,640,478 A * | 6/1997 | Roller | .................. | G02B 6/3869 |
| | | | | 385/92 |
| 6,960,028 B2 * | 11/2005 | Lampert | .............. | G02B 6/3859 |
| | | | | 385/81 |
| 9,304,271 B2 * | 4/2016 | Dietrich | ............... | G02B 6/4292 |
| 2009/0299352 A1 * | 12/2009 | Zerfas | ..................... | A61B 18/22 |
| | | | | 606/15 |
| 2016/0282604 A1 * | 9/2016 | Yoshino | ............. | G02B 23/2469 |
| 2018/0000645 A1 * | 1/2018 | Scheller | .............. | A61F 9/00823 |

* cited by examiner

*Primary Examiner* — Rhonda S Peace
(74) *Attorney, Agent, or Firm* — The PL Law Group, PLLC

(57) ABSTRACT

A vascular optical fiber guidewire includes an optical fiber guidewire and a plug connected to the optical fiber guidewire. The plug may be a memory alloy plug including a handle, a fixing groove and a sleeve which are sequentially connected. A radius of a segment of the fixing groove is larger than a radius of a segment of the fixing groove. The fixing groove cooperates with an external connector to provide a locking effect. The sleeve is provided with an elastically deformable spiral structure. The memory alloy plug is sleeved on a metal tube sleeved outside the optical fiber guidewire and connected with the optical fiber guidewire. A part of the metal tube extending from the memory alloy plug forms a spiral shape by spirally cutting to protect and support the optical fiber guidewire. The insertion and extraction operations and rotating operations can be facilitated.

10 Claims, 12 Drawing Sheets

VASCULAR OPTICAL FIBER GUIDEWIRE WITH PLUG

CROSS REFERENCE TO RELATED APPLICATIONS AND CLAIM OF PRIORITY

The present application is a continuation application to International Application No. PCT/CN2019/105100 with an International Filing Date of Sep. 10, 2019 which claims the benefit of Chinese Patent Application No. 201910735056.4 filed in the Chinese Intellectual Property Office on Aug. 9, 2019, the entire contents of which are incorporated herein by reference.

BACKGROUND

1. Technical Field

The present disclosure relates to the technical field of medical instruments, specifically to a vascular optical fiber guidewire with a plug, and more specifically to a vascular optical fiber guidewire with a memory alloy plug.

2. Background Art

Photodynamic Therapy (PDT) is a new technology for the diagnosis and treatment of diseases by using photodynamic effect. This therapy is based on the photodynamic effect. It belongs to a photosensitization reaction accompanied with biological effects in which oxygen molecule is involved, and comprises the following processes: a photosensitizer absorbed by a tissue is excited by the irradiation of a specific wavelength of laser; and then the energy, by the photosensitizer in the excited state, is transferred to oxygen in the surrounding environment, to generate highly active singlet oxygen; an oxidation reaction occurs between the singlet oxygen and adjacent biomacromolecules, so as to produce cytotoxicity, which in turn leads to cell damage or even death. Compared with traditional therapies, photodynamic therapy has many advantages including small trauma, good targeting, no drug resistance and side effects.

Usually visible red light is used for irradiation. Most of photosensitizers can strongly absorb light with a wavelength of 630 nm or greater than 630 nm. Laser is the most convenient and portable light source, and has coherence and mono-chromaticity. That is, a laser source can produce a single wavelength of light with the high energy. In addition, an output power of the laser source can be precisely regulated, and laser produced thereby can be directly introduced into hollow organs, penetrating into tumors through fiber optical cables. Diode lasers are often used because they are cheaper than metal-vapor lasers or tuned-dye lasers, and are portable. The photodynamic treatment time is related to the light absorbing ability of the photosensitizers and the effectiveness of energy transfer between light and oxygen. Compared with conventional treatments such as surgery, chemotherapy and radiotherapy, photodynamic therapy of tumor has several advantages, such as small trauma, low toxicity, good targeting and good applicability. However, the way of irradiation is limited to the body surface or big channels, and due to the limits from the laser emission mechanism and pharmacological properties of photosensitizers, the photodynamics of photodynamic therapy may only work on the area of a few millimeters, which greatly limits its application in the medical field.

At present, Seldinger arterial intubation technique is very mature. Under the guidance of clinical imaging medicine (X-ray, CT, MR, B-us, etc.), a delicate instrument, such as a special catheter or guidewire, is inserted into a lesion via percutaneous vascular route or an original channel in human body, so as to achieve a diagnostic imaging and treatment. This technique uses a metal guidewire via percutaneous vascular route to enter blood vessels and reach the lesion. This method is simple in operation, slight in damage, and does not need to suture blood vessels. Thus, it completely replaces previous methods which need to cut open the blood vessels surgically, and becomes a basic operation technique of modern interventional radiology. This method has achieved good effects in tumor thrombosis and drug perfusion, intra-arterial irradiation, prevention of radiation damage, chemotherapy, preoperative embolization of tumor blood vessels, vasoactive drugs and alcohol perfusion, etc.

A vascular optical fiber guidewire is an interventional guidewire for guiding a laser beam within blood vessels. The vascular optical fiber guidewire generally has an optical fiber, a metal spiral tube surrounding the optical fiber, and a polymer coating on the outer surface. The vascular optical fiber guidewire generally has only a diameter of only a few hundred micrometers and can be rotated and bent. Therefore, the vascular optical fiber guidewire, like a guidewire can be guided to pass through blood vessels and in turn enter human organs by the medical imaging, and simultaneously transmits the laser required for photodynamic therapy.

An optical fiber connector (also known as an optical fiber adapter or flange) is a device for performing detachable connection (action) between optical fibers. It precisely mates two end faces of two optical fibers, so that the optical energy output from the transmitting optical fiber can be maximally coupled to the optical receiving fiber and the impact on the system due to its involvement in the optical link can be minimized. The optical fiber connector also affects the reliability and performance of optical transmission system to some extent.

In the actual application, the optical fiber connector can be classified based on the structure. Here are some of common optical fiber interfaces and optical fiber connectors.

i. FC Type Connector

The FC (Ferrule Connector) type connector is a round metal joint with threads, and fastened by a turnbuckle. Generally, the FC (Ferrule Connector) type connector is used on the ODF (common in patch panel), and a nut thereof is screwed onto the adapter. This type of connector has advantages including firm, dustproof, and disadvantages including long installation time.

ii. SC Type Connector

The SC type connector is a snap-in plastic square connector. The structures and sizes of a pin and a coupling sleeve are the same as those of the FC type connector. An end surface of the pin is mostly polished by means of PC or APC. This type of connector uses plug-and-pull way for fastening without rotating. The SC type connector can be directly plugged and unplugged, and thus is convenient in use. However, the SC type connector has the disadvantage of being easy to fall out. Generally, it is used at the optical interface of the transmitting device. 1×9 optical module and GBIC optical module all use the SC type connector.

iii. ST Type Connector

The ST type connector is a snap-in metal joint with round housing and uses a turnbuckle for fastening. The ST type connector is commonly used in optical fiber patch panel. It can be fixed by rotating the ST head for half a rotation into a bayonet after inserting. However, the ST type connector has the disadvantage of being easily broken.

iv. LC Type Connector

The LC type connector is a small square plastic connector that is similar as the SC type connector in shape, but smaller. It is made with a convenient modular jack (RJ) latch mechanism. The LC type connector is used in the SFP module. At present, in terms of the single mode SFF, LC type connector has occupied a dominant position, and also is widely used in the application of multimode.

v. MT-RJ Type Connector

The MT-RJ type connector is a square precision plastic rubber connector. It starts in the MT connector developed in NTT, and is made with the same type of latch mechanism as RJ-45 LAN electrical connector. Guide pins are installed on both sides of the small casing for the alignment of optical fiber. The MT-RJ interface has the size which is the same as that of a standard phone, and can be installed in the RJ-45 panel and patch panel module. In order to facilitate connection with the optical transceiver, the connector end surface fiber is a two-core (interval of 0.75 mm) arrangement design, and is the next generation high-density fiber optic connector mainly used for data transmission.

vi. Biconic Connector

The most representative product of this type connector is developed by Bell Laboratory of the United States. This product consists of two plugs with precision-molded ends of frusto-conical cylindrical shape and a coupling assembly with a double-tapered plastic sleeve inside.

Most of the above fiber optical connectors are used in the field of optical communication, and the transmission power of laser is not high. The connector is connected with common optical fibers, but cannot be directly connected with the vascular optical fiber guidewire. In addition, the convenience and safety for inserting and removing the connector cannot meet the requirements in the medical application.

SUMMARY

In view of the above, an object of the present disclosure is to provide a vascular optical fiber guidewire with a plug.

The present disclosure provides a vascular optical fiber guidewire with a plug. The vascular optical fiber guidewire includes an optical fiber guidewire and a plug connected to one end of the optical fiber guidewire. The plug is a memory alloy plug; the memory alloy plug includes a handle, a fixing groove and a sleeve which are sequentially connected. A radius of a segment of the fixing groove connected to the handle is larger than a radius of a segment of the fixing groove connected to the sleeve. The fixing groove is configured to cooperate with an external connector, so as to provide a locking effect. The sleeve is provided with an elastically deformable spiral structure.

Preferably, the sleeve includes a first sleeve and a second sleeve. The elastically deformable spiral structure is disposed between the first sleeve and the second sleeve. The elastically deformable spiral structure is made by spirally cutting a memory alloy.

Preferably, the optical fiber guidewire is threaded through an axial center of the memory alloy plug. A gap is disposed between the optical fiber guidewire and the sleeve.

Preferably, the vascular optical fiber guidewire further includes a jack set capable of cooperating with the memory alloy plug. The jack set includes a main body. In an axial direction of the main body, a connecting optical fiber is disposed at an axial center inside one end of the main body, and a cavity capable of accommodating the memory alloy plug is disposed at an axial center inside other end of the main body.

The main body is sleeved with an elastic pin. The elastic pin is capable of locking the memory alloy plug when the memory alloy plug is attached to the jack set.

Preferably, the elastic pin includes a connecting portion connectable to the main body. Both ends of the connecting portion are symmetrically connected to an elastic portion. Ends of two elastic portions are respectively provided with a fixing portion inwardly. The fixing portions are parallel to the connecting portion. Each of the two elastic portions is sequentially inclined inward from a rear end to a front end, so that the elastic pin has a small diameter at the front end and a large diameter at the rear end.

The main body extends into the elastic pin from the connecting portion and extends out from between the two fixing portions at the end having the small diameter of the elastic pin.

Preferably, two opposite sides of the main body are provided with openings penetrating through an inner side and an outer side of the cavity. When the elastic pin is closed, the two fixing portions are respectively engaged with the two openings.

When the memory alloy plug is inserted into the cavity, the fixing groove is located at the opening, and the fixing portion is engaged with the fixing groove to lock the memory alloy plug.

Preferably, the main body of the elastic pin is sleeved with a rolling ring for rolling or sliding along the main body. The rolling ring moves on the main body to deform the elastic pin, so as to insert or release the memory alloy plug.

Preferably, an end face of the fixing portions are inclined sequentially inward from a front end to a rear end, and forms a inclined face structure having a large diameter at the front and a small diameter at the rear end. The inclined face structure can be matched with the fixing groove.

Preferably, one end of the jack set is connected with the memory alloy plug, and other end of the jack set is connected with a fiber extension cable, a standard SMA905 plug or an FC/PC plug.

Preferably, the vascular optical fiber guidewire further includes a light-emitting portion capable of emitting light. The optical fiber guidewire has one end connected with the memory alloy plug, and other end connected with the light-emitting portion.

The present disclosure has the following advantages.

The vascular optical fiber guidewire of the present disclosure realizes the connection between the memory alloy plug and a laser or other devices, which facilitates the insertion and extraction operations, and rotating operations can also be performed for the optical fiber after the insertion without affecting coupling efficiency. Compared with a common plug, the memory alloy plug of the disclosure has greater elastic deformability and can be used repeatedly. The matching structure formed by the memory alloy plug and the elastic pin of the disclosure has a flexibility to ensure the proper matching of the optical fiber, and does not be broken due to fatigue during multiple using. In addition, the present disclosure is ingeniously designed with a structure formed by the memory alloy plug and the jack set. This structure can be tightly connected, and is convenient for connection and operation. Importantly, the structure of the present disclosure can reaches better optical fiber connection effect and high optical transmission power. The light-emitting portion capable of emitting light is disposed at one end of the optical fiber guide wire into the human body, so that the light

DETAILED DESCRIPTION

The experimental methods used in the following examples are conventional methods unless otherwise specified.

The materials, reagents and the like used in the following examples are commercially available unless otherwise specified.

Example 1

Figure 16:
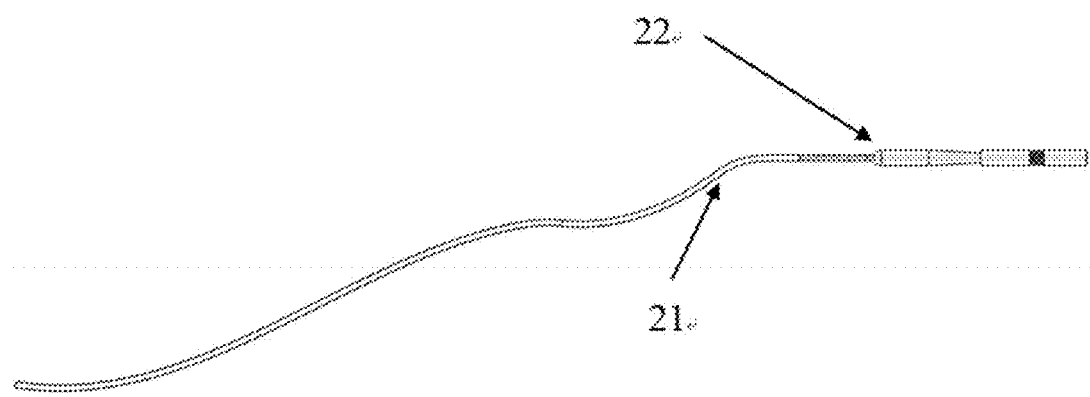
FIG. 16 is a schematic diagram illustrating the structure of a vascular optical fiber guidewire with a memory alloy plug.

FIG. 16 is a schematic diagram illustrating the structure of a vascular optical fiber guidewire with a memory alloy plug according to the present disclosure. One end of the optical fiber guidewire 21 is connected with the memory alloy plug 22. The arrangement of the memory alloy plug 22 allows the vascular optical fiber guidewire connecting with other optical fibers to achieve the extension thereof, or allows the vascular optical fiber guidewire to be easily connected to a laser to introduce a laser into the optical fiber guidewire 21. The overall shape of the memory alloy plug 22 may be a cylindrical or cylindrical-like shape with a circular or elliptical cross-section.

Figure 10:
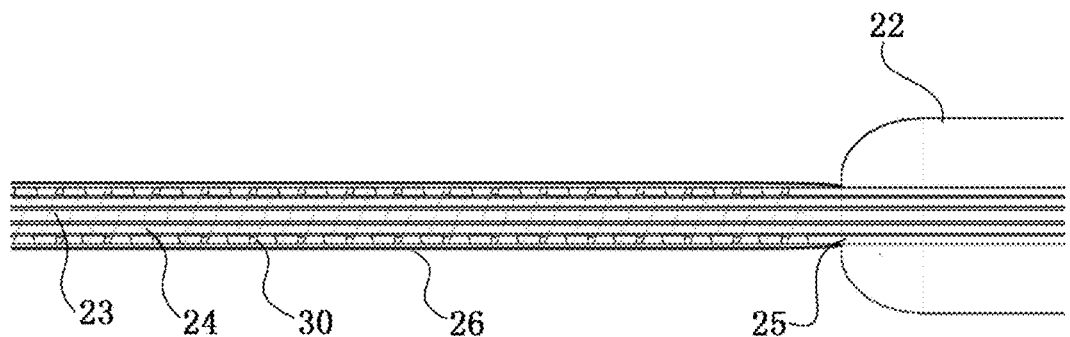
FIG. 10 is a schematic diagram illustrating the structure of the vascular optical fiber guidewire of FIG. 9.
Figure 11:
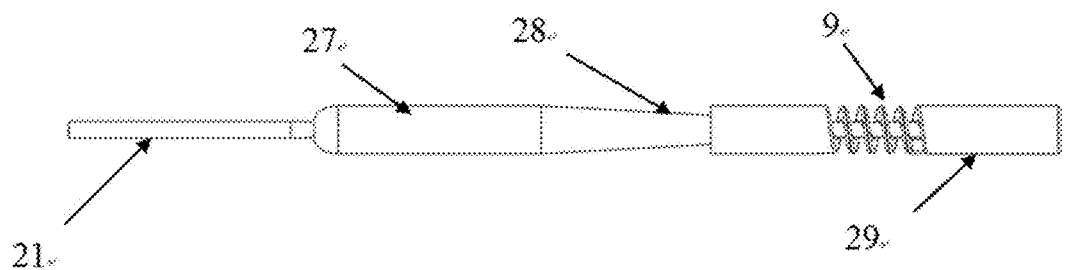
FIG. 11 is a schematic diagram illustrating the structure of the memory alloy plug of FIG. 9.

The structure of the optical fiber guidewire 21 is as shown in FIG. 10, and the memory alloy plug 12 is as shown in FIG. 11. The optical fiber guidewire 21 includes an optical fiber core wire 23 and an optical fiber cladding layer 24.

The optical fiber guidewire 21 includes an optical fiber wire 210 that includes the optical fiber core wire 23 and the optical fiber cladding layer 24.

The memory alloy plug 22 is composed of a handle 27, a fixing groove 28, and a sleeve 29. The handle 27 is a hand-held operating portion. A radius of a segment of the fixing groove 28 connected to the handle 27 is larger than a radius of a segment of the fixing groove 28 connected to the sleeve 29. That is, the fixing groove 28 is a truncated cone structure with the outer diameter being gradually decreasing from one end (i.e., the end connected with the handle 27) to the other end (i.e., the one end connected with the sleeve 29). Specifically, the end of the fixing groove connected to the handle 27 has a large diameter, and the end of the fixing groove connected to the sleeve 29 has a small diameter. The fixing groove 28 is configured to cooperate with an external connector, so as to provide a locking effect. The sleeve 29 is provided with an elastically deformable spiral structure 9, and the elastic deformable spiral structure 9 may be disposed at an intermediate position of the sleeve 29. That is, the sleeve 29 is divided into two parts by the elastic deformable spiral structure 9 which is just located between the two parts. The elastic deformable spiral structure 9 is composed of a plurality of spiral coils, and made by spirally cutting a memory alloy material, such as a nickel-titanium alloy or a copper-zinc alloy. The elastic deformable spiral structure made by using the memory alloy has high deformability, and may be used repeatedly.

Figure 12:
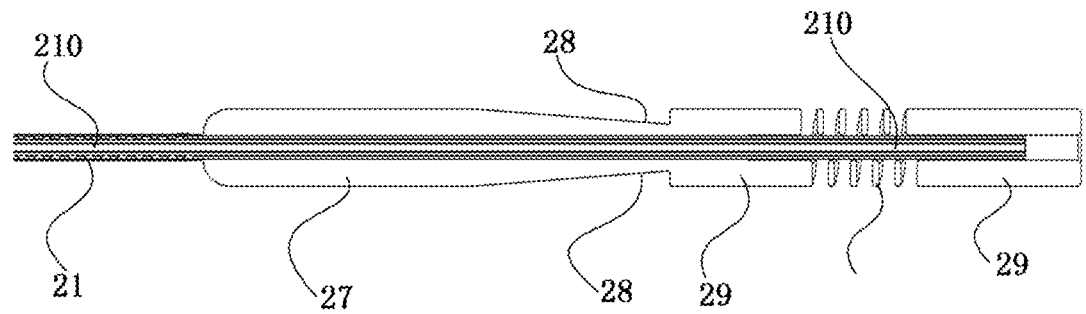
FIG. 12 is a cross-sectional diagram of the memory alloy plug of FIG. 9.

The optical fiber wire 210 extends through the memory metal plug 22. In other word, the memory metal plug 22 wraps around the optical fiber wire 210, as shown in FIG. 12. It is preferred that a small gap is provided between the optical fiber wire 210 or the optical fiber guidewire 21 and the sleeve 29. When the sleeve 29 is extended or contracted due to force, the sleeve 29 will slide longitudinally along the optical fiber guidewire 21 or the optical fiber wire.

Figure 13:
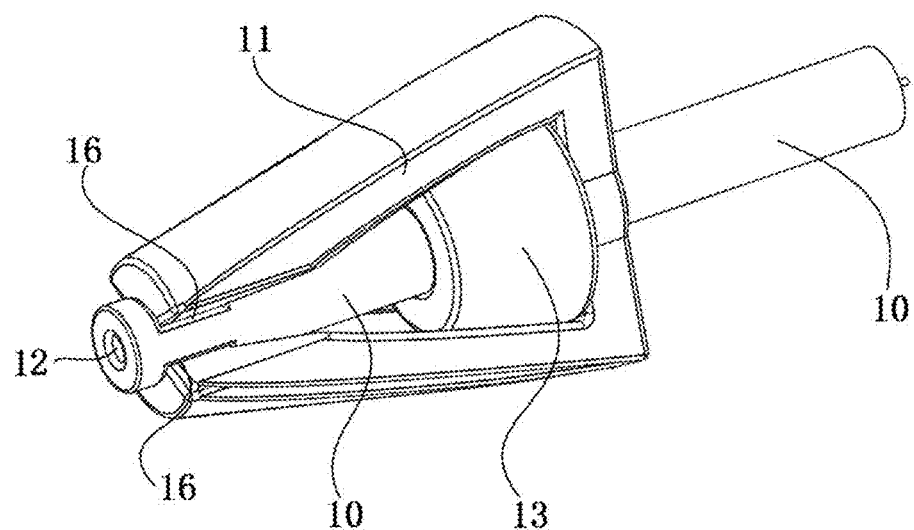
FIG. 13 is a schematic diagram illustrating a structure of jack set.

The memory alloy plug 22 can be inserted into the jack set (as shown in FIG. 13). The jack set includes the main body 10. In an axial direction of the main body 10, a connecting optical fiber 14 is disposed at an axial center inside one end of the main body 10, and a cavity 12 capable of accommodating the memory metal plug 22 is arranged at an axial center inside the other end of the main body 10, so that when the memory alloy plug 22 is inserted into the cavity, the optical fiber wrapped at the axial center of the memory alloy plug 22 is exactly aligned with the connecting optical fiber 14, and the optical fiber wire is brought into contact with or close to the connecting fiber 14. Therefore, light may be transmitted from the connecting fiber 14 to the optical fiber wire, causing high transmission efficiency. An elastic pin 11 is sleeved on the main body 10, so that when the memory alloy plug 22 is inserted into the cavity 12 of the main body 10, the elastic pin 11 may be snapped into the fixing groove 28, so as to be fixed to the memory metal plug 22.

Figure 14:
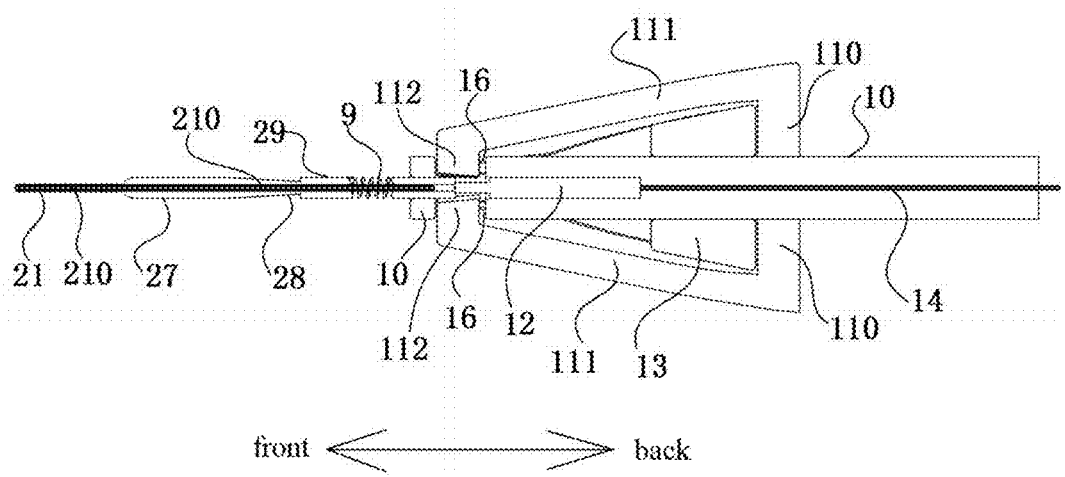
FIG. 14 is a cross-sectional diagram illustrating the structure that the memory alloy plug is inserting into the jack set.
Figure 15:
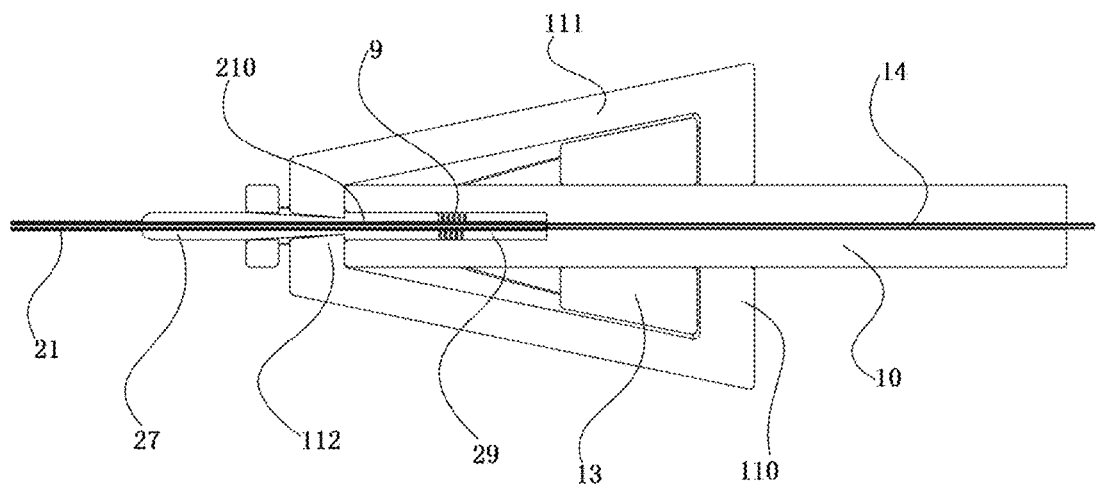
FIG. 15 is a cross-sectional diagram illustrating the structure that the memory alloy plug has been inserted into the jack set.

Referring to FIGS. 13-15, the elastic pin 11 includes a connecting portion 110 that can be connected to the main body 10. Both ends of the connecting portion 110 are symmetrically connected with an elastic portion 111 having elasticity. Ends of two elastic portions 111 are respectively provided with a fixing portion 112 inwardly. The fixing portions 112 are parallel to the connecting portion 110. Each of the two elastic portions 111 is sequentially inclined inward from a rear end (i.e., the end connected to the connecting portion) to a front end (i.e., the end connected to the fixing portion), so that the elastic pin 11 has a small diameter at the end of the fixing portion 112 and a large diameter at the end of the connecting portion 110. The main body 10 extends into the elastic pin 11 from the connecting portion 110 and extends out from between the two fixing portions 112 at the end having the small diameter of the elastic pin. In addition, the main body 10 of the elastic pin is sleeved with a rolling ring 13. The rolling ring 13 can roll or slide along the main body 10. And the rolling ring 13 moves on the main body 10 to deform the elastic pin 11, so as to insert or release the memory alloy plug 22.

As shown in FIG. 13-15, two opposite sides of the main body 10 are provided with openings 16 penetrating through an inner side and an outer side of the cavity. Two openings 16 are respectively disposed corresponding to the two fixing portions 112. In the natural state of the elastic pin (when the elastic pin is closed), the two fixing portions 112 are respectively located at the openings 16 on both sides of the main body 10, and the rolling ring 13 is located at the end with the large diameter of the elastic pin. An outer diameter of the rolling ring 13 is the same as the inner diameter of the end with the large diameter of the elastic pin 11.

Since the elastic pin 11 possesses a flat tapered structure or a flat truncated cone structure, and has an inner diameter that is also reduced from the front end to the rear end, the outer diameter of the rolling ring 13 gradually will apply an outward force to the elastic portion 111 when the rolling ring 13 is moved toward the end with small diameter of the elastic pin (i.e., the direction toward the fixing portion 112), so that the elastic portion 111 is opened and the fixing portion 112 comes out from the opening 16, and the force against the elastic portion 111 will disappear when the rolling ring 13 is moved toward the rear end, so that the elastic portion 111 rebounds to the original position and the fixing portion 112 returns to the opening 16, i.e., the elastic pin 11 is closed.

Preferably, the end face of the fixing portion 112 is an inclined face that may be matched with the end face of the fixing groove 28. In other word, the inclined face is inclined inward sequentially from the front end to the rear end, forming a structure having a large diameter at the front end and a small diameter at the rear end. When the sleeve 29 of the memory metal plug 22 is inserted into the cavity 12, the inclined surfaces (i.e., the end face) of the two fixing portions 112 are exactly located in the fixing groove 28, so that the cooperation therebetween is safely and securely.

As shown in FIGS. 14-15, the main body 10 has a connecting optical fiber 14 at the axial center inside. When the memory alloy plug 22 is inserted into the cavity 12 of the jack set, the sleeve 29 will lift the fixing portion 112 up at the opening 16 when passing through the opening 16, while the fixing portion 112 will drive the elastic portion 111 to spring up, i.e., the elastic pin 11 is opened under the pushing of the sleeve 29, the sleeve 29 of the memory alloy plug 22 enters the insertion hole 12. When the memory alloy plug 22 is inserted to the full depth of the jack hole, the pitches of the elastic deformable spiral structure 9 of the memory alloy plug 22 contracts due to force, the fixing groove 28 is exactly located at the opening 16, and the fixing portion 112 is exactly snapped into the fixing groove 28, so that the elastic pin 11 is snapped by the fixing groove 28 of the memory metal plug 22 and the optical fiber wire inside the optical fiber guidewire is docked with the connecting fiber 14 of the jack set to realize coupling. The inclined face of the fixing portion 112 is inclined sequentially inward from the front end to the rear end, which also facilitates the sleeve 29 to smoothly extend through the opening and to lift the fixing portion 112 up.

The connecting optical fiber 14 may be connected to a laser. In use, the optical fiber guidewire enters the body and reaches affected sites such as tumor tissues at the liver through blood vessels; then a laser is emitted from the laser, is transmitted to the optical fiber wires through the connecting optical fiber 14, and is exited from an end of the optical fiber wires to reach the affected sites of human body, so as to achieve the required treatment. When the treatment with laser is completed, the laser is turned off; the rolling ring 13 is pushed toward the fixing portion 112 to force the elastic pin 11 opening, so that the memory alloy plug 22 is sprang from the cavity 12 under the elastic deformation spiral force. In this example, compared with a common metal plug, the memory alloy plug of the disclosure has greater elastic deformability and may be used repeatedly without changing the accuracy. Moreover, the matching structure of the spiral and the elastic pin in the elastic deformable spiral structure 9 has such a flexibility to ensure the proper matching of the optical fiber, and does not break due to fatigue during multiple using. This example brings out good comprehensive effects.

Preferably, a metal tube 25 is provided at the center of the memory alloy plug 22. The metal tube 25 extends in the direction of the optical fiber guidewire and is wrapped around the periphery of the optical fiber wires. The spiral tube 30 is located at the periphery of the optical fiber wires and formed by spirally cutting metal tube, and thus may be used for supporting or protecting the optical fiber guidewire 21. A polymer coating 26 is provided outside the spiral tube 30, which increases the lubricity and biocompatibility of the optical fiber guidewire 21 in the blood and reduces the resistance.

It should be noted that the metal tube 25 may wrap around all of optical fibers (or the optical fiber guidewire 21) penetrated inside the memory metal plug. In this situation, a small gap is provided between the sleeve 29 and the metal tube 25, so that when the sleeve 29 is extended and contracted due to force, the sleeve 29 may slide along the metal tube 25.

In this example, the vascular optical fiber guidewire is connected to the laser or other optical fibers, devices through the memory alloy plug. That is, the jack set has one end connected to the optical fiber guide wire 21 through the memory alloy plug, and the other end connected to an optical fiber extension cable, the laser or other devices including plugs (such as standard SMA905 plugs, FC/PC plugs). Therefore, the extension of the fiber guidewire or the connection of fiber guidewire and laser may be achieved.

Example 2

Figure 9:
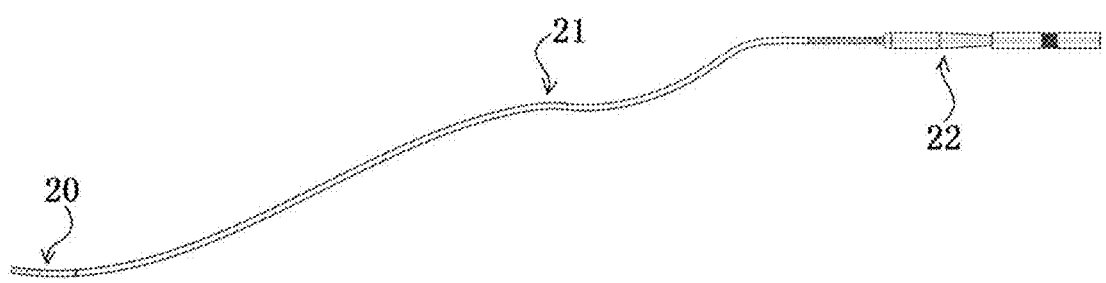
FIG. 9 is a schematic diagram illustrating the structure of a vascular optical fiber guidewire with a memory alloy plug according to the present disclosure.

One end of the optical fiber guidewire 21 (i.e., the end left outside the body) is connected to the memory alloy plug 22 described in Example 1, and other end (i.e., the end inside of the human body) of the optical fiber guidewire is connected to a light-emitting portion 20 capable of emitting light, as shown in FIG. 9. The optical fiber guidewire 21 may be connected to the light-emitting portion 20 by many means, such as welding, integral molding, removable connection and any other conventional connection methods in the art. In addition, the optical fiber of the light-conducting portion is paired with the optical fiber of the light-emitting portion to transmit all of the optical energy to the optical fiber of the light-emitting portion. The optical fibers are preferably integrally formed, so as to achieve high light transmission efficiency. The specific condition may be determined according to actual conditions.

Figure 1:
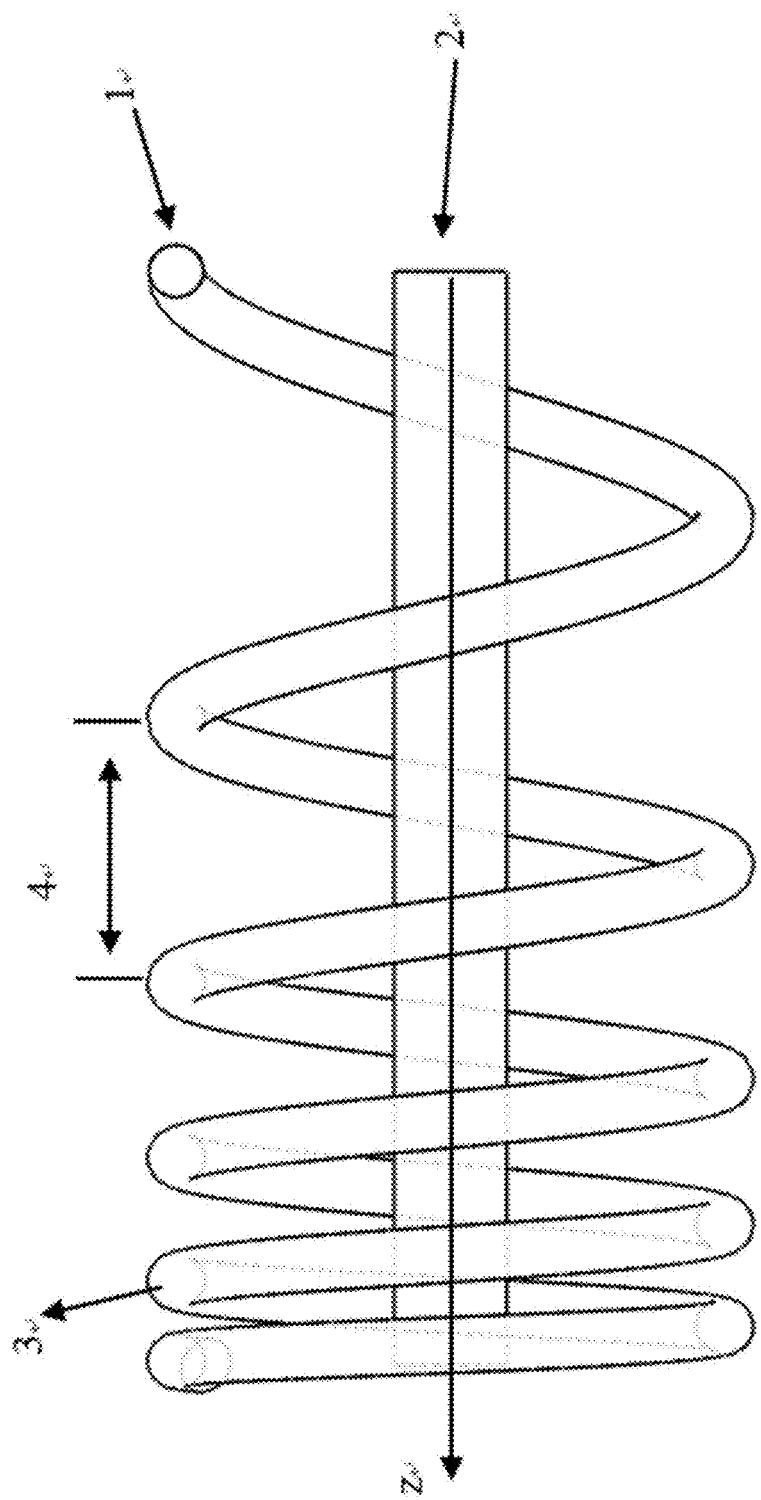
FIG. 1 is a schematic diagram illustrating the structure of a vascular optical fiber guidewire with a side illuminated.

FIG. 1 is a schematic structural view of a light-emitting portion. The light-emitting portion 20 includes a metal axial wire 2 and an optical fiber 1 surrounding the metal axial wire. The optical fiber 1 includes a core wire and a cladding layer covering the core wire. The optical conductivity of the cladding layer is smaller than that of the core wire. In normal circumstances, light can only be transmitted from the core wire and cannot be scattered from the cladding layer. This is a kind of light-conducting device that restrains the transmission of light in the core wire by comparing refractive index of the core wire with that of the cladding layer (e.g., the refractive index of the core wire is 1.5, and the refractive index of the cladding layer is 1.3).

In the light-emitting portion, if a bending radius of the optical fiber 1 around the metal axial wire is less than a critical bending radius, the cladding layer will be unable to restrain the light transmitted in the core wire, causing light to leak from the side wall by passing through the cladding layer, this phenomenon is called as side-illumination; if the bending radius of the optical fiber around the metal axial wire is greater than the critical bending radius, the light is only transmitted in the core wire, and cannot pass through the cladding layer and leak from the side wall. In practical applications, when the optical fiber of the light-emitting portion is spirally wound around the periphery of the metal axial wire, it may have different bending radiuses at different positions. For example, the bending radius is smaller than the critical bending radius at where the side-illumination is required; and the bending radius is greater than the critical bending radius at where the side-illumination is not required. Of course, it is also possible to exit light at various positions of the optical fiber as needed, or even every positions of the optical fiber.

A length of the optical fiber guide wire 21 may be 0.1 m to 2 m, such as 1.6 m, and a length of the light-emitting portion may be 10 mm to 100 mm, such as 50 mm, depending on actual requirements.

In this example, the bending radius R of the optical fiber includes a value of the critical bending radius Rc. The critical bending radius Rc is a minimum radius at which the cladding layer may directly restrains the light transmitted in the core wire, resulting in light not leaking from the side wall. Specifically, in the light-emitting portion, when the pitch surrounded by the optical fiber is reduced and the bending radius R of the optical fiber is smaller than Rc, light will leak from the cladding layer and scatter into the surrounding environment through the side wall. The pitch of the optical fiber around the metal axial wire is a variable. When this variable has a suitable value as the axial fiber changes radially, the light scattered from the side wall will have a constant intensity, achieving a uniform side-illumination.

In this example, a bending loss at the bend of the optical fiber is the optical power of the light exited from the bending side face, and the relationship between the bending loss and the bending radius of the optical fiber is as shown in formula I:

$$\alpha_c = A_c R^{-1/2} \exp(-UR) \qquad \text{formula I}$$

where $$A_c = \frac{1}{2}\left(\frac{\pi}{a}\right)^{1/2} 3.7 \left(\frac{\lambda_c}{\lambda}\right)^2 \qquad \text{formula I-1}$$

$$U \approx 0.705 \frac{\Delta n^{3/2}}{\lambda}\left(2.748 - 0.996\frac{\lambda}{\lambda_c}\right)^3 \qquad \text{formula I-2}$$

In the formula I, the formula I-1, the formula I-2, $\alpha_c$ represents the power loss per unit length of the single-mode fiber in dB; R represents the bending radius of the optical fiber in mm; $A_c$ represents the parameters related to the optical fiber structure in $dB/m^{1/2}$; a represents the radius of core wire of the optical fiber in μm; $\lambda_c$ represents the cutoff wavelength of the fiber transmission in nm; $\Delta n$ represents the refractive index difference between the core wire and the cladding layer.

In the formula I-1, $$k_0 = \frac{2\pi}{\lambda},$$

$k_0$ is the vacuum wave number, $\lambda$ represents the transmission wavelength of the optical fiber;

$$\lambda_c = \frac{2\pi a}{V_c}\sqrt{n_1^2 - n_2^2},$$

and $n_1$ and $n_2$ respectively represent the refractive index of the core wire and cladding layer of the optical fiber; Vc represents the cutoff frequency, Vc=2.40483.

The bending radius of the optical fiber is related to the angle between the spiral line of the optical fiber and the side line of the cylinder that is formed by winding the spiral line with radius r, and is calculated according to formula II:

$$R = \frac{4\pi^2 r^2 + (2\pi r \cdot \cot(\theta))^2}{4\pi^2 r} \qquad \text{formula II}$$

In formula II, R represents the bending radius of the optical fiber, θ represents the angle between the spiral line and the side line of the cylinder, and r represents the winding radius of the spiral of the optical fiber.

The relationship between the longitudinal length of the winding of the optical fiber and the angle between the spiral line of the optical fiber and the side line of the cylinder that is formed by winding the spiral line with radius r is calculated according to formula III:

$$-\frac{\ln(10)}{10}\alpha_c(\theta(z)) \cdot \cos(\theta(z)) \cdot (-s_0 \cdot z + s_1) = -s_0 \qquad \text{formula III}$$

In formula III, z represents the longitudinal length of the optical fiber along the metal axial wire, θ represents the angle between the spiral line and the side line of the cylinder; $\alpha_c$ represents the power loss per unit length of the single-mode fiber in dB; $s_1$ represents the initial power, $s_0$ represents the rate of power attenuation.

The optical power exited from the side face of the optical fiber is calculated according to formula IV:

$$P(z) = \frac{s_0}{\frac{\ln(10)}{10}\alpha_c(\theta(z))\cdot\cos(\theta(z))} \quad \text{formula IV}$$

P(z) represents the optical power exited from the side face of the optical fiber, i.e., the distribution of the optical power on the longitudinal length of the fiber along the metal axial wire; z represents the longitudinal length of the fiber along the metal axial wire; θ represents the angle between the spiral line and the side line of the cylinder; $\alpha_c$ represents the power loss per unit length of a single-mode fiber in dB.

Through the above formulas, the characteristic of the emitted light (such as optical power, bending loss), bending radius and so on can be calculated through different parameters. The corresponding formula can be selected according to the parameters that need to be obtained or calculated, which is convenient and quick.

In addition, in this example, the light-emitting portion may be set to emit light only on one side. That is, when the optical fiber 1 is located on the light-emitting side of the light-emitting portion and the bending radius thereof is smaller than the critical bending radius, light-emitting positions at each spiral coil will be connected together to form a line parallel to the axis z of the optical fiber guidewire, which is equivalent to the light-emitting positions being distributed along the axis z of the optical fiber guidewire. Referring to FIG. 1, the light-emitting positions are all located at the top of each spiral coil, i.e., the position indicated by light scattering point 3. In practical applications, light is usually set to be emitted along the axis z on one or both sides of the optical fiber guide wire.

In this example, the structure of the optical fiber guidewire includes, but is not limited to, any one of i) to v): i) Like the structure of the light-emitting portion, the optical fiber guide wire includes a metal axial wire and an optical fiber wire surrounding the metal axial wire. The optical fiber wire also includes an optical core wire and an optical fiber cladding layer wrapped around the periphery of the optical core wire. The bending radius of the optical fiber wire is greater than the critical bending radius, so that the light can only be confined to transmit in the optical core wire and cannot be scattered from the optical fiber cladding layer. The main function of the light-conducting portion is to conduct light. ii) The optical fiber guide wire only includes the optical fiber wire. The optical fiber wire includes an optical core wire and an optical fiber cladding layer wrapped around the periphery of the core wire. The light can only be transmitted in the optical core wire and scattered from the end face, and cannot be emitted from the side face. iii) The optical fiber guide wire includes the optical fiber wire and a polymer layer or metal layer wrapped around the optical fiber wire. iv) The optical fiber guide wire includes an optical fiber wire and a metal wire spirally wound around the fiber of the conducting portion. Of course, a polymer layer may be coated outside the metal wire. v) The optical fiber guide wire may be similar to the optical fiber structures involved in other patents previously filed by the applicant. In order to distinguish it from the terms of the fiber, the core wire, the cladding layer and the like of the light-emitting portion, this paragraph uses the term optical fiber, the optical core wire, and the optical fiber cladding layer to define the optical fiber structure of the optical fiber guide wire 21, to avoid confusion.

In this example, in use, one end of the light-emitting portion of the optical fiber guide wire enters the body, and the end having the memory alloy plug remains outside the body.

Example 3

On the basis of Example 2, when the optical fiber 1 is bent, if the bending radius of the bending portion is less than Rc (critical bending radius is a minimum radius at which the cladding layer can directly restrains the light transmitted in the core wire, resulting in light not leaking from the side face), the cladding layer will be unable to restrain the light from transmitting in the core wire, causing light to leak from the side face. The present disclosure utilizes the principle to construct a structure that the metal axial wire is surrounded by the optical fiber. In the part where the optical fiber guide wire is used to transmit light, i.e., the part where a side-illumination is not required, the rotating pitch of the optical fiber is large, and thus the bending radius thereof will be much larger than Rc. Therefore, light cannot be exited from the cladding layer and is restrained to transmit inside the cladding layer. In the areas where light is required to be scattered, such as the head portion of the optical fiber guidewire, the pitch of the optical fiber is reduced and the bending radius of the fiber is reduced to be less than Rc, light will leak from the cladding layer and scatter into the surrounding environment. The pitch of the optical fiber around the metal axial wire is a variable. When this variable has a suitable value as the axial fiber z (See FIG. 2) changes radially, the light scattered from the side face will have a constant intensity, achieving a uniform side-illumination.

The bending of the optical fiber causes the leak of light from the cladding layer. The leak of light reduces the optical power transmitted in the core wire, resulting in bending loss of the transmission power.

The loss per unit length is calculated according to the bending loss of the single-mode fiber formula (1):

$$\alpha_c = A_c R^{-1/2} \exp(-UR) \quad (1)$$

where $$A_c = \frac{1}{2}\left(\frac{\pi}{aW^3}\right)\left[\frac{u}{Wk_1(W)}\right]^2$$

$$U = \frac{4\Delta nW^3}{3aV^2 n_2}$$

$\alpha_c$ represents the loss per unit length of the single-mode fiber in dB; a and Δn respectively represent the radius of the core wire and the difference of refractive index between the core wire and the cladding layer; u, W and V respectively represent the radial normalized phase constant, radial normalized decay constant and normalized frequency. The formulas are shown as follows:

$$u^2 = a^2(n_1^2 k_0^2 - \beta_z^2)$$

$$W^2 = a^2(\beta_z^2 - n_2^2 k_0^2)$$

$$V = ak_0(n_1 - n_2)^{1/2} \approx ak_0(2n_2\Delta n)^{1/2}$$

where $k_0$ represents vacuum wave number:

$$k_0 = \frac{2\pi}{\lambda},$$

$\beta_z$ is the propagation constant in the z direction.

According to the transmission equation of the optical fiber, some characteristic parameters of the optical fiber transmission can be obtained:

Cutoff frequency: $V_c = 2.40483$

Cutoff wavelength:

$$\lambda_c = \frac{2\pi a}{V_c}\sqrt{n_1^2 - n_2^2}$$

V and W are represented by the above characteristic parameters as:

$$V = 2.405\frac{\lambda_c}{\lambda}$$

$$W = 1.1428V - 0.996 \approx 2.7484\frac{\lambda_c}{\lambda} - 0.996.$$

The approximate expression of U in $m^{-1}$ can thus be obtained:

$$U \approx 0.705\frac{\Delta n^{3/2}}{\lambda}\left(2.748 - 0.996\frac{\lambda}{\lambda_c}\right)^3.$$

In addition, $$\frac{W^{-\frac{2}{3}}u^2}{W^2 K_1^2(W)}$$

can be simplified to $$3.7\left(\frac{\lambda_c}{\lambda}\right)^2,$$

and thus $$A_c = \frac{1}{2}\left(\frac{\pi}{a}\right)^{1/2} 3.7\left(\frac{\lambda_c}{\lambda}\right)^2,$$

its unit is $$dB/m^{\frac{1}{2}}.$$

Based on the above, the relationship between the bending loss formula of the single-mode fiber and the bending radius R is obtained.

Assuming that the length of the optical fiber is L, depending on the bending loss, the relationship among the bending loss, the exited power and the incident power is as follows:

$$\alpha_c \cdot L = -10\log\left(\frac{P(L)}{P(0)}\right) = \frac{-10}{\ln(10)}\ln\left(\frac{P(L)}{P(0)}\right).$$

Here, a log of a base-10 logarithm is transformed into the natural logarithm ln. $P(0)$ is the incident optical power and $P(L)$ is the exited optical power. Then, there is shown as below.

$$P(L) = P(0) \cdot \exp\left(-\frac{\ln(10)}{10}\alpha_c \cdot L\right).$$

When $\alpha_c$ changes with the change of the length L due to the change of the pitch, the above formula may be in the differential form:

$$dP(L) = -\frac{\ln(10)}{10}\alpha_c \cdot P(L)dL. \tag{2}$$

In addition, due to the change of pitch, the optical fiber winding length L is not proportional to the longitudinal length z. However, it is required to make the illumination along z-axis as uniform as possible, rather than to obtain uniform illumination along the fiber winding length L. Therefore, it is necessary to transform the relationship between L and z.

Figure 2:
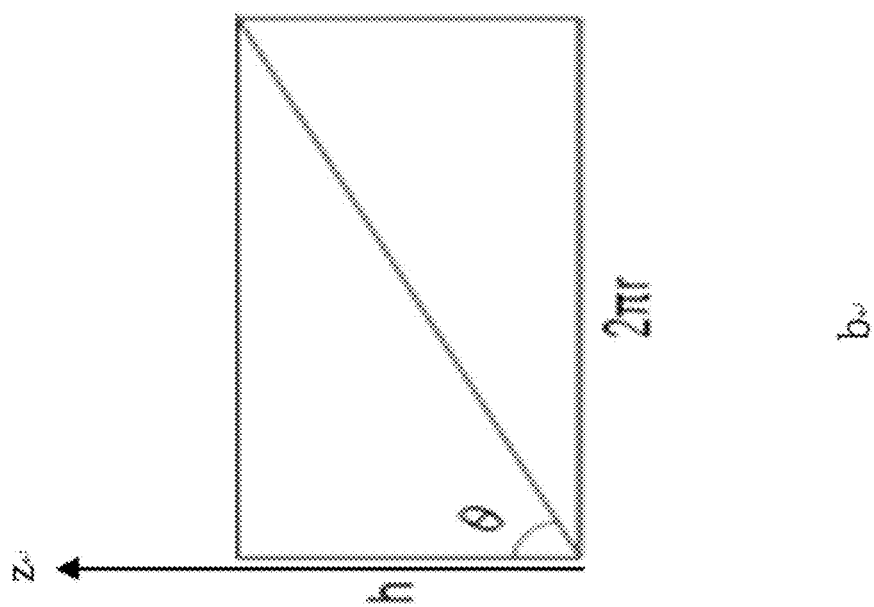
FIG. 2 is a schematic diagram illustrating the expansion of spiral structure according to the side surface of cylinder.
Figure 2:
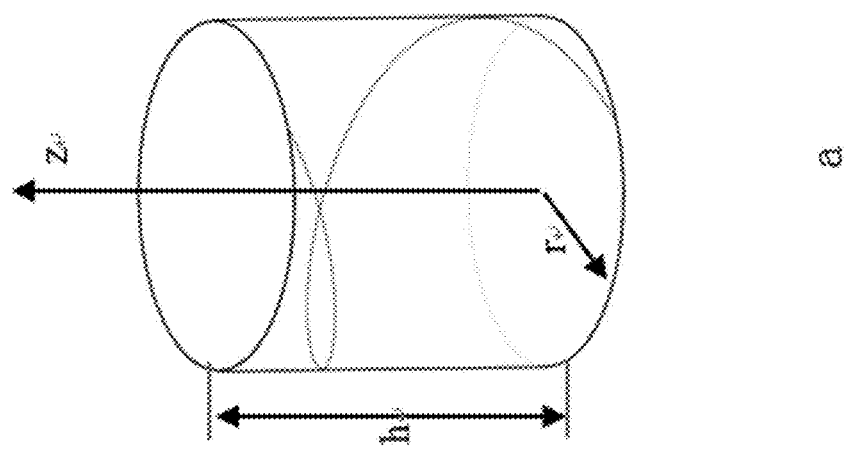

As shown in a of FIG. 2, the spiral line is wound around a cylinder of radius r, and the pitch is h. If the side surface of the cylinder is expanded into a plane, as shown in b of FIG. 2, the angle between the spiral line and the side line of the cylinder will be θ. When this angle θ changes and the pitch of the spiral line changes, the radius of curvature R will also change.

The relationship among the radius of curvature, pitch h and the surround radius r of the spiral line is $$R = \frac{4\pi^2 r^2 + h^2}{4\pi^2 r}.$$

As $h = 2\pi r \cdot \cot(\theta)$, it will be that $$R = \frac{4\pi^2 r^2 + (2\pi r \cdot \cot(\theta))^2}{4\pi^2 r}.$$

Thus, the curvature radius R of the optical fiber, or $\alpha_c$ is only related to the variable angle θ. In addition, L and z have the following relationship:

$$dl = \cos(\theta)dz.$$

Thus, $$dP(z) = -\frac{\ln(10)}{10}\alpha_c(\theta(z)) \cdot P(z)\cos(\theta(z))dz \tag{3}$$

Here, both L and θ are ultimately expressed as function of z.

The final result of the power variation in the optical fiber is $$\frac{dP(z)}{dz} = -s_0. \tag{4}$$

Power is linearly attenuated at a constant rate as z increases. The attenuated light exits from the side face of the optical fiber, and the exited optical power is distributed along the length z at a constant rate.

The above formula is integrated to obtain:

$$P(z) = -s_0 \cdot z + s_1.$$

The physical meaning of the above formula is that: at z=0, the initial power is $s_1$, and the rate of power attenuation is $s_0$. The formula (4) in the differential form can be transformed to:

$$dP(z) = \times s_0 dz.$$

Compared with the formula (3), the following formula can be obtained:

$$-\frac{\ln(10)}{10} \alpha_c(\theta(z)) \cdot P(z) \cos(\theta(z)) = -s_0. \quad (5)$$

When the expression of P(z) is brought into the formula (5), the below formula can be obtained:

$$-\frac{\ln(10)}{10} \alpha_c(\theta(z)) \cdot \cos(\theta(z)) \cdot (-s_0 \cdot z + s_1) = -s_0. \quad (6)$$

The above formula is the transcendental formula of the implicit function of the $\theta(z)$ function with respect to the variable z. The relationship between $\theta(z)$ and z can be obtained by numerical solution.

Specifically, the above calculation evolution can be illustrated by the following parameters.

Assuming that the power of the laser at the incident end of the optical fiber is 1 W, i.e., P(0)=1, the power at the exit end is 0 W (i.e., light is totally scattered), the length of the metal axial wire of the spiral optical fiber is 50 mm (0.05 m), i.e., P(z=0.05)=0, it will obtain that $s_0$=20, $s_1$=1.

The single-mode fiber has a core wire radius of 4.5 μm, a cladding layer diameter of 125 μm, the he refractive index of $n_1$=1.445593 and $n_2$=1.444687, the radius of the fiber around the cylinder of 200 μm, and the transmission wavelength of 652 nm.

Figure 3:
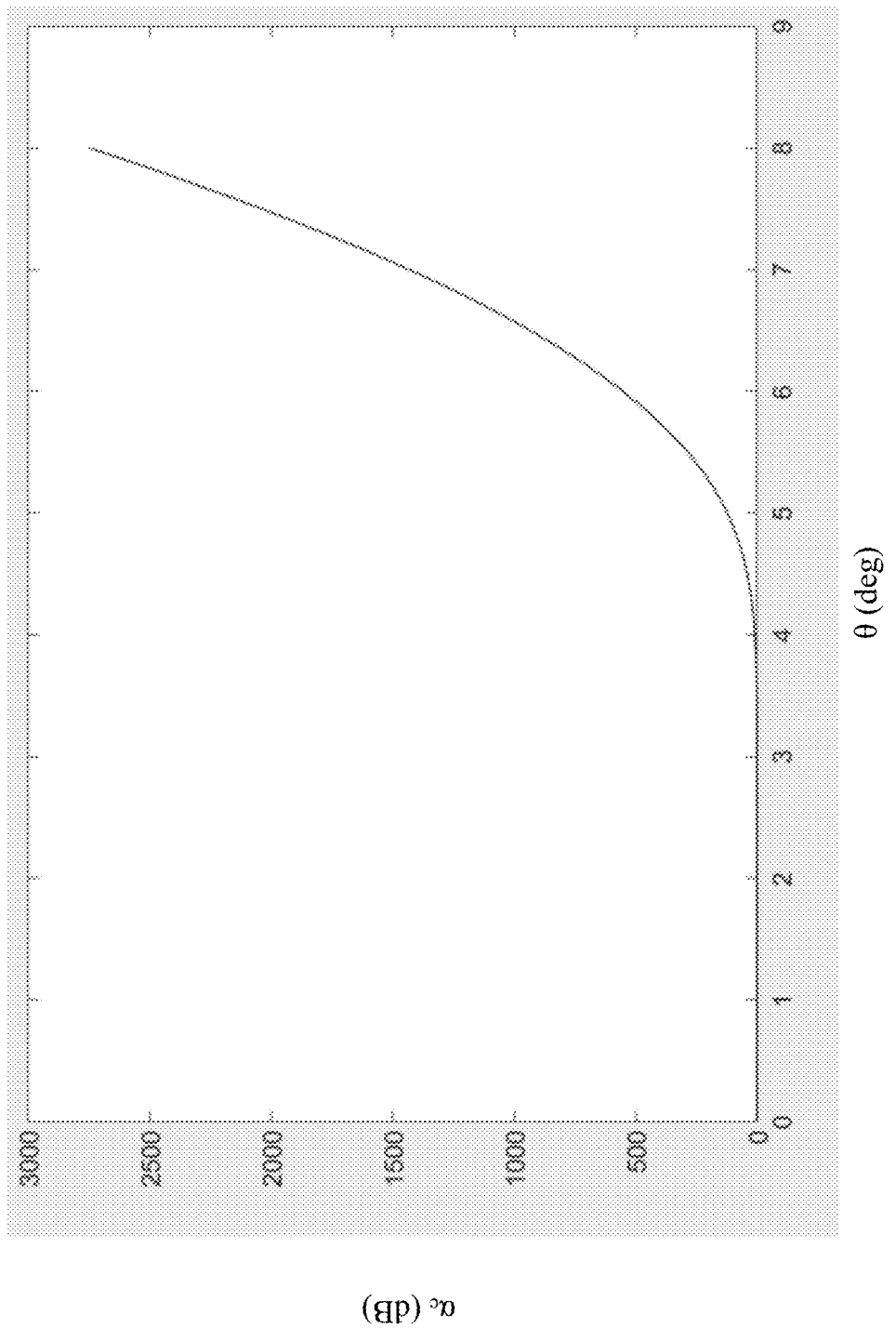
FIG. 3 shows the relationship between the fiber bending loss $\alpha_c$ and $\theta$.

According to the above parameters, if the angle θ of the optical fiber spiral is changed from 0 to 8 degrees, as shown in FIG. 3, the loss will rise sharply at about 4 degrees. By using this great change, light can be scattered from the core wire.

Figure 4:
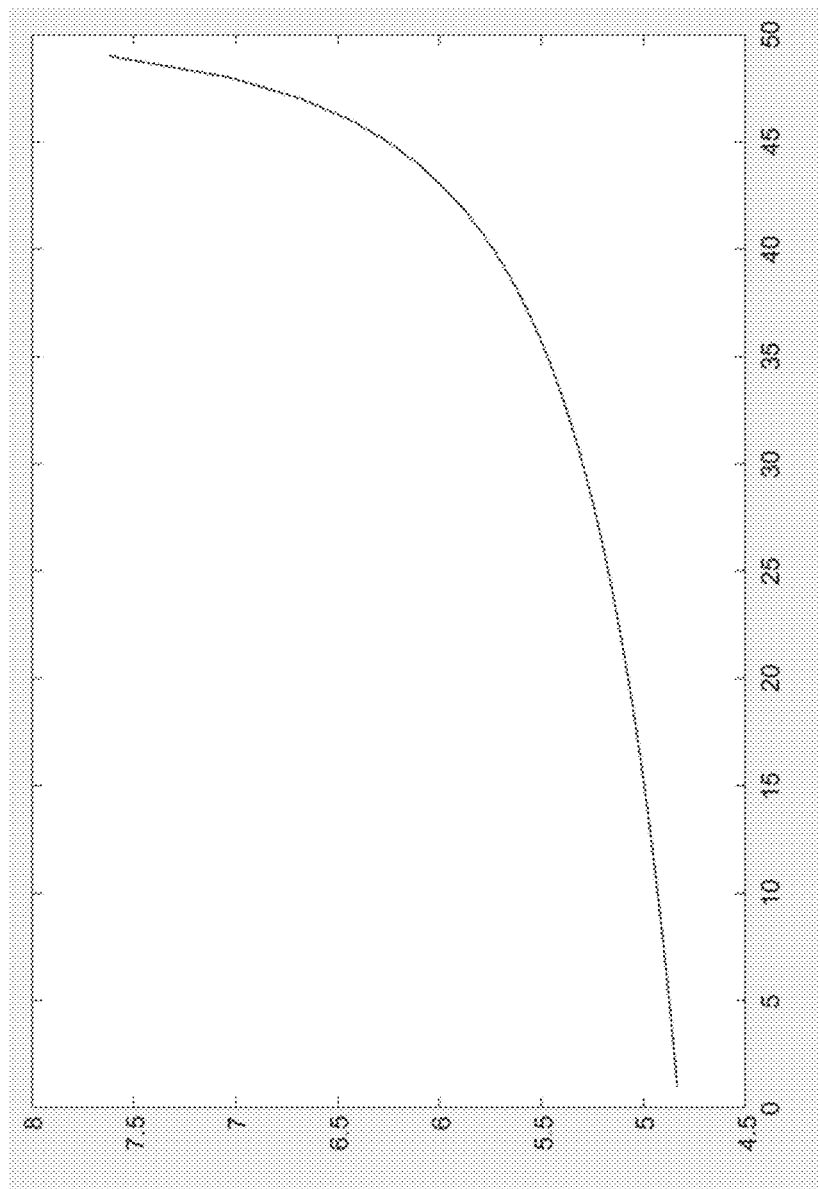
FIG. 4 shows the relationship between $\theta$ and z.

The above parameters are brought into formula (6), and the value of θ corresponding to each z is obtained by a numerical algorithm (for example, a dichotomy or an iterative method), as shown in FIG. 4.

The angle θ of the optical fiber rotation along the axis is set based on the data calculated in FIG. 4, and then a spiral shape of optical fiber with a veritable pitch will be obtained.

According to formula (5), the variation in power can be shown as follows $$P(z) = \frac{s_0}{\frac{\ln(10)}{10} \alpha_c(\theta(z)) \cdot \cos(\theta(z))}$$

Figure 5:
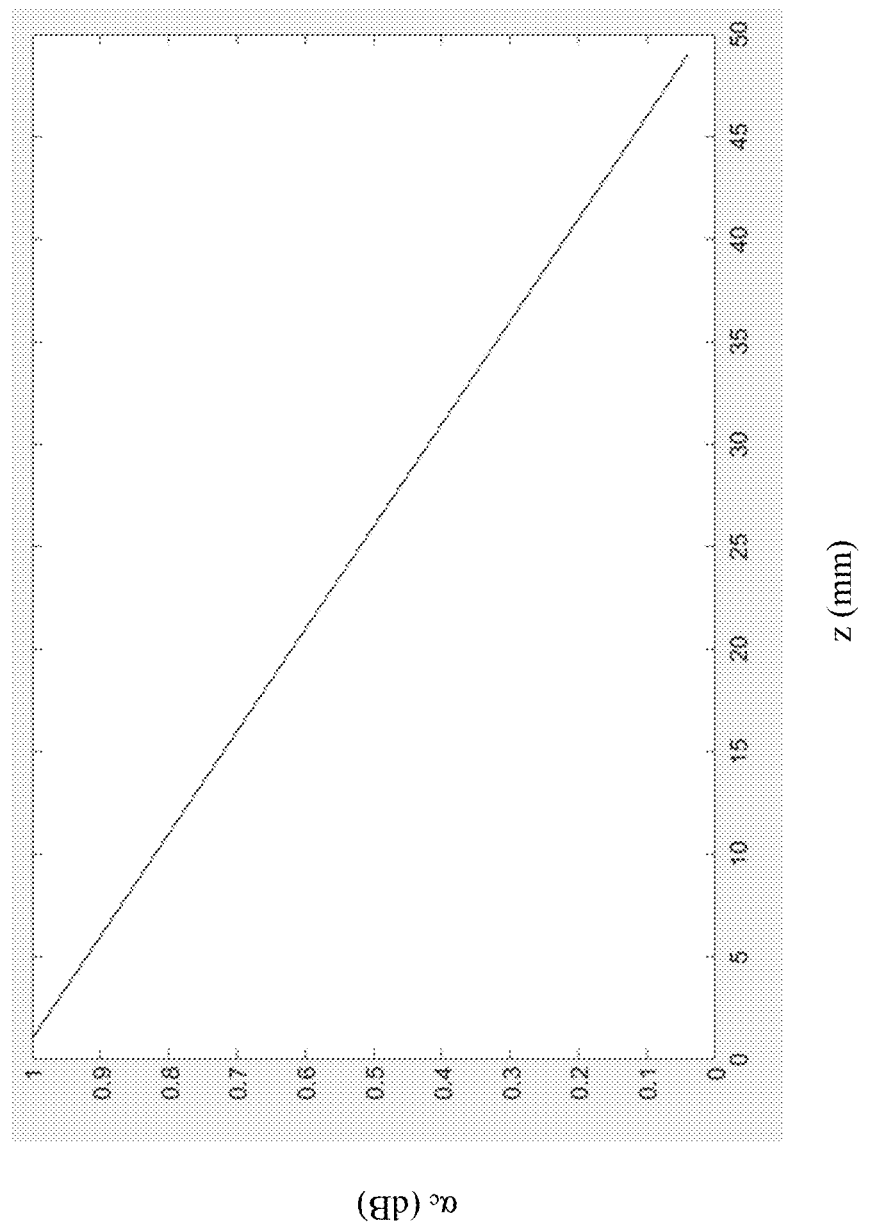
FIG. 5 shows the attenuation of power in optical fiber with z.

When bring the calculated θ(z) mentioned in the above into this formula, it will obtain the relationship between power and z, as shown in FIG. 5.

From the above, the followings can be known.

1. The bending loss of the transmission power of the optical fiber due to the bending around the metal axial wire is the optical power of the light exited from the bending side.

The relationship between the bending loss of the single-mode fiber and the bending radius of the optical fiber is calculated according to formula (1):

$$\alpha_c = A_c R^{-1/2} \exp(-UR) \quad (1);$$

where $$A_c = \frac{1}{2}\left(\frac{\pi}{a}\right)^{1/2} 3.7 \left(\frac{\lambda_c}{\lambda}\right)^2 \quad \text{formula (1)-1}$$

$$U \approx 0.705 \frac{\Delta n^{3/2}}{\lambda} \left(2.748 - 0.996 \frac{\lambda}{\lambda_c}\right)^3 \quad \text{formula (1)-2}$$

In the formula (1), the formula (1)-1, the formula (1)-2, $\alpha_c$ represents the power loss per unit length of the single-mode fiber in dB; R represents the bending radius of the optical fiber in mm; $A_c$ represents the parameters related to the optical fiber structure in $dB/m^{1/2}$; a represents the radius of core wire of the optical fiber in μm; $\lambda_c$ represents the cutoff wavelength of the fiber transmission in nm; Δn represents the refractive index difference between the core wire and the cladding layer.

In the formula I-1, $$k_0 = \frac{2\pi}{\lambda},$$

$k_0$ is the vacuum wave number, where λ represents the transmission wavelength of the optical fiber;

$$\lambda_c = \frac{2\pi a}{V_c} \sqrt{n_1^2 - n_2^2},$$

where $n_1$ and $n_2$ respectively represent the refractive index of the core wire and cladding layer of the optical fiber; $V_c$ represents the cutoff frequency and $V_c$=2.40483.

2. The bending radius of the optical fiber is related to the angle between the spiral line of the optical fiber and the side line of the cylinder that is formed by winding the spiral line with radius r, and is calculated according to formula II:

$$R = \frac{4\pi^2 r^2 + (2\pi r \cdot \cot(\theta))^2}{4\pi^2 r};$$

in formula II, R represents the bending radius of the optical fiber, θ represents the angle between the spiral line and the side line of the cylinder, and r represents the spiral winding radius of the optical fiber.

3. The relationship between the longitudinal length of the optical fiber and the angle between the spiral line of the optical fiber and the spiral line of the optical fiber and the side line of the cylinder that is formed by winding the spiral line with radius r is calculated according to formula III:

$$-\frac{\ln(10)}{10}\alpha_c(\theta(z))\cdot\cos(\theta(z))\cdot(-s_0\cdot z+s_1)=-s_0. \quad \text{formula III}$$

In formula III, z represents the longitudinal length of the optical fiber along the metal axial wire, θ represents the angle between the spiral line and the side line of the cylinder; $\alpha_c$ represents the power loss per unit length of the single mode fiber in dB; $s_1$ represents the initial power, $s_0$ represents the rate of power attenuation.

4. When bringing θ(z) obtained from formula III into the following formula IV, the optical power exited from the side face of the optical fiber can be calculated:

$$P(z)=\frac{s_0}{\frac{\ln(10)}{10}\alpha_c(\theta(z))\cdot\cos(\theta(z))} \quad \text{formula IV}$$

P(z) represents the optical power exited from the side face of the optical fiber, i.e., the distribution of the optical power on the longitudinal length of the fiber along the metal axial wire; z represents the longitudinal length of the fiber along the metal axial wire; θ represents the angle between the spiral line and the side line of the cylinder; $\alpha_c$ represents the power loss per unit length of a single-mode fiber, in dB.

In the above-mentioned vascular optical fiber guidewire, the pitch of the optical fiber to be set can be calculated by bringing the angle between the spiral line and the side line of the cylinder obtained from formula II or formula III into formula V:

$$h=2\pi r\cdot\cot(\theta) \quad \text{Formula V.}$$

In formula V, h represents the pitch of the optical fiber, r represents the spiral winding radius of the optical fiber, and θ represents the angle between the spiral line and the side line of the cylinder. In a specific example, the length of the light-conducting portion of the optical fiber guide wire is 1.6 m. The side-illuminated structure is started at the distance of 50 mm from the top end (i.e., the light-emitting portion, the length of z in the formula). The radius r is 200 μm. According to the above formula, the relationship between the angle θ between the spiral line and the side line of the cylinder and z obtained is as shown in FIG. 4. If h and R is known, according to h=2πr·cot(θ), $$R=\frac{4\pi^2 r^2+(2\pi r\cdot\cot(\theta))^2}{4\pi^2 r}$$

can be calculated.

FIG. 5 shows the power attenuation in the optical fiber 1 caused by the exit of light from the cladding layer, which is due to the gradual decrease of the bending radius of the optical fiber with the variable pitch helical fiber design described above. This indicates that the exit rate of light along z is constant.

Figure 6:
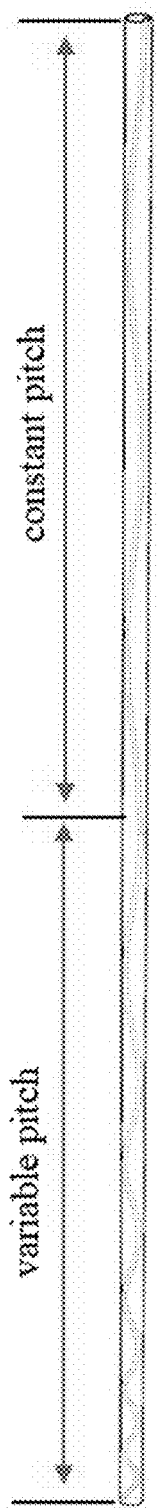
FIG. 6 shows optical fiber guidewires with a constant pitch and a variable pitch.

Further, as shown in FIG. 6, in the main light conducting portion of the optical fiber guide wire, it is not necessary to leak light from the cladding layer, and thus the pitch is set to a value much larger than the critical bending radius Rc; and in the top of the optical fiber guide wire, such as at where from the top 50 mm, the pitch is set to gradually decrease, and the value is changed according to the relationship shown in FIG. 4, and thus light with a constant intensity will scatter from the top along the side face.

Figure 7A:
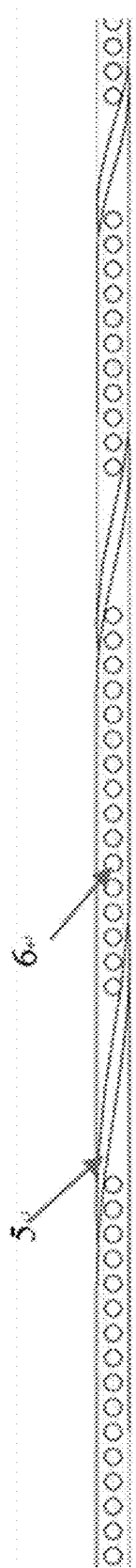
FIG. 7A is a schematic diagram illustrating the structure of the axial wire.
Figure 7B:
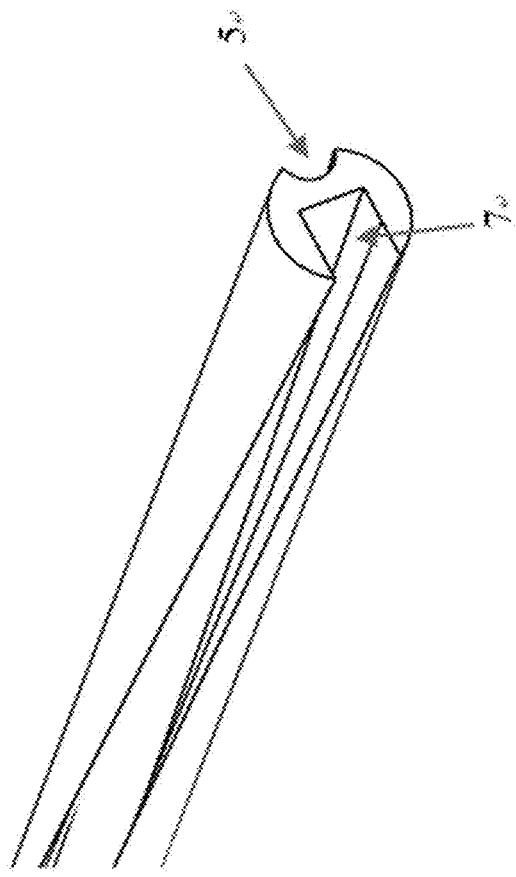
FIG. 7B is a schematic diagram illustrating another structure of the axial wire.
Figure 8:
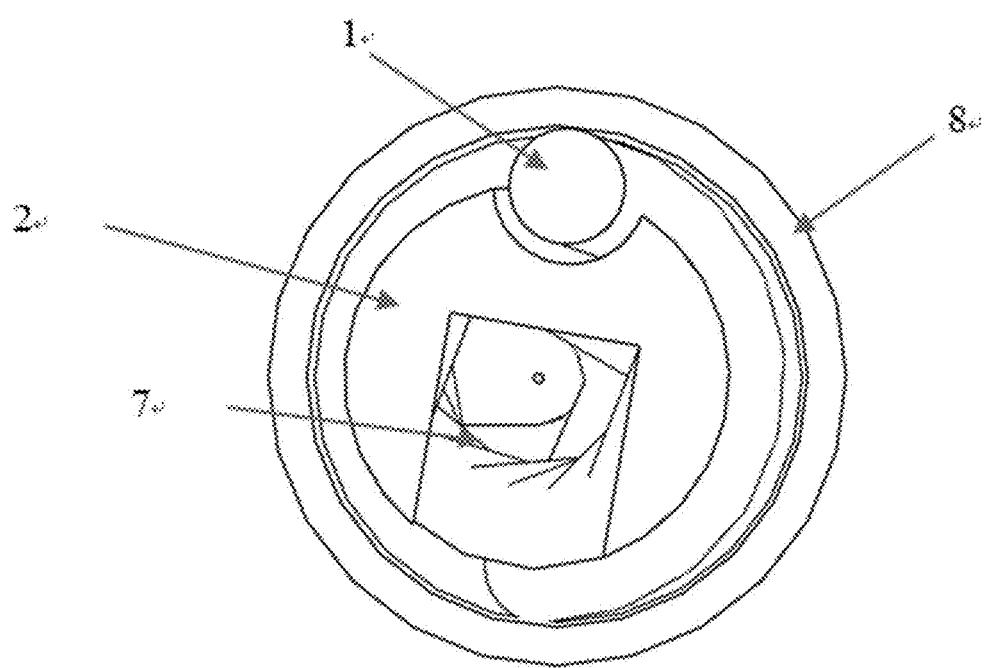
FIG. 8 is a schematic cross-sectional view illustrating an optical fiber guidewire.

Further, the metal axial wire 2 may be a diameter of 50 μm to 1 mm. In order to increase the winding tightness of the optical fiber 1, spiral groove 5 as shown in FIGS. 7A and 7B may be provided on the metal axial wire 2, so as to embed the optical fiber 1 in spiral groove 5. In order to increase the flexibility of the metal axial wire 2, a hole-like structure (such as, the hole 6) as shown in FIG. 7A may be processed on the side face of the metal axial wire 2 to lower the hardness of the metal axial wire 2. It is also possible to process a longitudinal spiral groove 7 as shown in FIG. 7B to lower the hardness of the metal axial wire 2.

Further, a polymer sleeve may be arranged outside the optical fiber guide wire, so as to increase the stability and safety of the overall structure. Moreover, a hydrophilic and/or hydrophobic coating 8 may be arranged outside the polymer sleeve, so as to reduce resistance of the vascular optical fiber guide wire in the blood and increases biocompatibility. A material of the polymer sleeve may be at least one selected from polyethylene, polyvinyl chloride, epoxy resin, aliphatic polyester, chitin and polylactic acid.

The optical fiber 1 of the present disclosure may be a quartz optical fiber, a polymer optical fiber or a glass optical fiber. A material of the cladding layer may also be quartz or the like, as long as the refractive index is lower than that of the optical fiber, so that light can be transmitted only in the optical fiber without being exited from the cladding layer.

Material of the metal axial wire 2 of the present disclosure may be stainless steel, aluminum alloy, titanium alloy or nickel titanium alloy, and may also be carbon fiber, polymer material or the like. The polymer material used is at least one selected from polyethylene, polyvinyl chloride, epoxy resin, aliphatic polyester, chitin and polylactic acid.

In the present disclosure, the terms "optical fiber wire 210", "optical fiber 1", "connecting optical fiber 14" and the like are named differently, but they have the same structure including the cross-sectional structure, and include a core for transmitting light and a cladding layer for restraining the transmission of light.

The above description is only a preferred embodiment of the present disclosure. It should be appreciated that various modifications and changes can be made to the present disclosure. Any modifications, equivalents, improvements, etc., made within the spirit and scope of the present disclosure, are intended to be included within the scope of the present disclosure.

What is claimed is:

1. A vascular optical fiber guidewire with a plug, comprising
   an optical fiber guidewire, and
   a plug connected to one end of the optical fiber guidewire, wherein the plug is a memory alloy plug comprising a handle, a fixing groove and a sleeve which are sequentially connected;
   a radius of a segment of the fixing groove connected to the handle is larger than a radius of a segment of the fixing groove connected to the sleeve;
   the fixing groove is configured to cooperate with an external connector, so as to provide a locking effect; and
   the sleeve is provided with an elastically deformable spiral structure.

2. The vascular optical fiber guidewire according to claim 1, wherein the sleeve comprises a first sleeve and a second sleeve; the elastically deformable spiral structure is disposed between the first sleeve and the second sleeve; the elastically deformable spiral structure is made by spirally cutting a memory alloy material.

3. The vascular optical fiber guidewire according to claim 2, wherein the optical fiber guidewire is threaded through an axial center of the memory alloy plug, and a gap is disposed between the optical fiber guidewire and the sleeve.

4. The vascular optical fiber guidewire according to claim 1, further comprising a jack set capable of cooperating with the memory alloy plug; the jack set comprises a main body; in an axial direction of the main body, a connecting optical fiber is disposed at an axial center inside one end of the main body, and a cavity capable of accommodating the memory alloy plug is disposed at an axial center inside other end of the main body;

the main body is sleeved with an elastic pin, and the elastic pin is capable of locking the memory alloy plug when the memory alloy plug is attached to the jack set.

5. The vascular optical fiber guidewire according to claim 4, wherein the elastic pin comprises a connecting portion connectable to the main body; both ends of the connecting portion are symmetrically connected to an elastic portion having elasticity; ends of two elastic portions are respectively provided with a fixing portion inwardly; the fixing portion is parallel to the connecting portion; both of the two elastic portions are sequentially inclined inward from a rear end to a front end, so that the elastic pin having a small diameter at the front end and a large diameter at the rear end is formed;

the main body extends through the elastic pin from the connecting portion, and extends out from between the two fixing portions at the end having the small diameter of the elastic pin.

6. The vascular optical fiber guidewire according to claim 5, wherein two opposite sides of the main body are provided with openings penetrating through an inner side and an outer side of the cavity; when the elastic pin is closed, the two fixing portions are respectively engaged with the two openings;

when the memory alloy plug is inserted into the cavity, the fixing groove is located at the openings, and the fixing portion is engaged with the fixing groove to lock the memory alloy plug.

7. The vascular optical fiber guidewire according to claim 6, wherein a rolling ring is sleeved on the main body of the elastic pin for rolling or sliding along the main body; the rolling ring moves on the main body to deform the elastic pin, so as to insert or release the memory alloy plug.

8. The vascular optical fiber guidewire according to claim 7, wherein an end face of the fixing portions are inclined sequentially inward from a front end to a rear end to form an inclined face structure having a large diameter at the front end and a small diameter at the rear end; and the inclined face structure is capable of cooperating with the fixing groove.

9. The vascular optical fiber guidewire according to claim 4, wherein the jack set has one end connected with the memory alloy plug, and other end connected with an optical fiber extension cable, a standard SMA905 plug or an FC/PC plug.

10. The vascular optical fiber guidewire according to claim 1, further comprising a light-emitting portion capable of emitting a light; the optical fiber guidewire has one end connected with the memory alloy plug, and the other end connected with the light-emitting portion.

* * * * *